United States Patent [19]

Träger et al.

[11] Patent Number: 4,492,754
[45] Date of Patent: Jan. 8, 1985

[54] COMPOSITION AND METHOD FOR THE DETERMINATION OF HYDROGEN PEROXIDE

[75] Inventors: Ulrich Träger, Limburgerhof; Bernward Sojka, Viernheim; Hans Lange, Lampertheim, all of Fed. Rep. of Germany

[73] Assignee: Boehringer Mannheim GmbH, Mannheim, Fed. Rep. of Germany

[21] Appl. No.: 387,392

[22] Filed: Jun. 11, 1982

[30] Foreign Application Priority Data

Jun. 23, 1981 [DE] Fed. Rep. of Germany ....... 3124594

[51] Int. Cl.³ .................... G01N 33/52; G01N 33/66; G01N 33/70; G01N 33/92
[52] U.S. Cl. ........................ 435/28; 422/56; 435/10; 435/11; 435/14; 435/17; 435/805; 436/135; 436/904
[58] Field of Search ......... 435/28, 10, 11, 14, 435/17, 805; 436/135, 904; 422/56

[56] References Cited

U.S. PATENT DOCUMENTS

| | | | |
|---|---|---|---|
| 4,247,297 | 1/1981 | Berti | 435/28 X |
| 4,247,631 | 1/1981 | Nix | 435/28 X |
| 4,260,679 | 4/1981 | Tsudd | 435/28 X |
| 4,278,439 | 7/1981 | White | 435/28 X |
| 4,367,285 | 1/1983 | Yamaguchi | 435/28 |
| 4,385,114 | 5/1983 | Guthlein | 435/28 |

FOREIGN PATENT DOCUMENTS

| | | |
|---|---|---|
| 7787 | 2/1980 | European Pat. Off. |
| 56-37556 | 4/1981 | Japan |

OTHER PUBLICATIONS

Chemical Abstracts, 95: 38670t (1981).

Primary Examiner—Sidney Marantz

Attorney, Agent, or Firm—Felfe & Lynch

[57] ABSTRACT

Composition for the detection of
(a) hydrogen peroxide or hydrogen peroxide forming substrates or
(b) peroxidases or peroxidatively reacting substances
which composition comprises a substrate capable of coupling and an oxidizable substance known to undergo the Trinder reaction, and
(a) a peroxidase or
(b) hydrogen peroxide
wherein the substrate capable of coupling is a compound of the formula

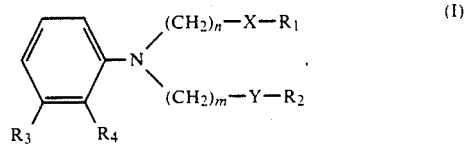

in which
n and m are individually selected from whole numbers of 1 to 4,
X and Y, which can be the same or different represent a valence bond or a phenylene radical,
$R_1$ and $R_2$ are individually selected from carboxyl or sulfonic acid groups and one of $R_1$ and $R_2$ can also be hydrogen or lower alkyl, and
$R_3$ and $R_4$ are individually selected from hydrogen and alkyl radicals of up to 6 carbon atoms;

and/or a salt of such compound.

The present invention also provides a method wherein the composition is brought together with a sample and the coloration obtained is evaluated visually or with a photometer.

17 Claims, No Drawings

COMPOSITION AND METHOD FOR THE DETERMINATION OF HYDROGEN PEROXIDE

This invention relates to methods and compositions for the determination of hydrogen peroxide or peroxidases. More specifically, the invention relates to such a method and composition utilizing oxidative coupling of chromogens in the presence of peroxidase and hydrogen peroxide.

The analytical determination of hydrogen peroxide is of considerable importance for medical diagnosis since, in the case of a large number of important detection processes, hydrogen peroxide is formed as an intermediate product which thereafter, by reaction with an appropriate chromogenic substance, preponderantly in the presence of a peroxidase (POD) as catalyst, is converted into an optically detectable substance. The extent of the formation of the optically detectable substance serves as a measure of the amount of hydrogen peroxide or as a measure of the amount of the hydrogen peroxide-forming substrate.

By reversing said reaction, i.e. adding hydrogen peroxide or a hydrogen peroxide forming substance, the concentration of peroxidases or peroxidatively reacting substances as hemoglobin can be estimated as well.

Numerous chromogens or indicator systems have been suggested for this reaction, one of the most frequently used indicator systems being that of Trinder (see Biochem., 6, 24-27/1969) in which phenol is oxidatively coupled with 4-amino-antipyrine in the presence of POD by the action of hydrogen peroxide to give a coloured material. Instead of the phenol, use can also be made of phenol derivatives, aniline derivatives, naphthol, naphthol derivatives, naphthylamine, naphthylamine derivatives or similary reacting substances. Instead of the 4-aminoantipyrine, use can also be made of other aminoantipyrine derivatives, vanillindiamine-sulphonic acid, methylbenzothiazolonehydrazone (MBTH), sulphonated methylbenzothiazolonehydrazone (S-MBTH) and similarly reacting substances.

An especially sensitive detection system is that described in Federal Republic of Germany Patent Specification No. 28 33 612 in which 4-aminoantipyrine is condensed by means of an N,N-dialkyl- or N-hydroxyalkyl-substituted 3-alkylaniline. The resulting coupling product displays a high molar extinction coefficient so that it is appropriately used for the detection of small amounts of hydrogen peroxide or of corresponding hydrogen peroxide-forming compounds respectively peroxidases or peroxidatively reacting substances. According to the above Patent Specification, the coloured materials produced by coupling with 4-aminoantipyrine are stable within normal measuring times but it was found that the aniline derivatives themselves, especially the preferred N-ethyl-N-hydroxyethyl-3-methylaniline (EHT), are not sufficiently storage stable and, especially in the case of impregnation on test strips, decompose within a few weeks. Furthermore, these compounds are liquid at ambient temperature so that they are also not very suitable for impregnation on to reagent carriers. Since they are weak bases, their crystalline salts with mineral acids can be used at pH values of below 6 but not in the range of from pH 6 to 8 which is especially interesting for diagnostic purposes.

The coupling of N-alkyl-N-hydroxyalkylanilines with benzothiazolinone hydrazones, especially 2-hydrazono-2,3-dihydro-3-methylbenzthiazole-6-sulphonic acid (S-MBTH), gives coloured materials with an especially high extinction so that S-MBTH could per se be used more advantageously than 4-aminoantipyrine for the detection of small amounts of hydrogen peroxide. However, the coloured materials obtained with EHT have been found to be unstable. In particular, superoxidations and other side effects occur, which result in a change of the absorption spectrum.

Therefore, the problem exists of finding a coupling component for an oxidative coupling which is stable even in the case of comparatively long storage in a finely divided state, for example when impregnated on to a reagent carrier or when in a reagent solution, is solid at ambient temperature in a pH range of 6 to 8 and in the case of the oxidative coupling gives coloured materials with a high molar extinction which are colour stable at least for an observation period of 1 hour so that the colour depth can serve as a measure of the amount of hydrogen peroxide or peroxidases to be detected.

Thus, according to the present invention, there is provided an agent for the detection of hydrogen peroxide or of hydrogen peroxide-forming substrates, respectively peroxidases or peroxidatively reacting substances, comprising a substrate capable of coupling and an oxidisable substance known for the Trinder reaction, a peroxidase respectively hydrogen peroxide or a hydrogen peroxide forming substance and optionally other additional materials known for the Trinder reaction, wherein, as substrate capable of coupling, it contains a compound of the general formula:

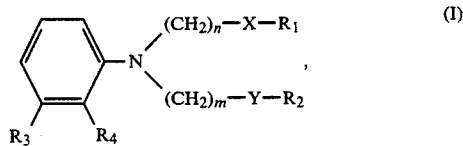

(I)

in which n and m, which can be the same or different, represent whole numbers of 1 to 4, X and Y, which can be the same or different, represent valency bonds or phenylene radicals, $R_1$ and $R_2$, which can be the same or different, represent carboxyl or sulphonic acid groups whereby one of $R_1$ and $R_2$ can also be a hydrogen atom or a lower alkyl radical and $R_3$ and $R_4$, which can be the same or different, represent hydrogen atoms or alkyl radicals containing up to 6 carbon atoms; and/or a salt thereof.

When $R_3$ and $R_4$ are alkyl radicals, they preferably contain 1 or 2 carbon atoms.

As components capable of oxidation, it is preferable to use 4-aminoantipyrine (4-AAP), 2-hydrazono-2,3-dihydro-3-methylbenzthiazole (MBTH) or especially 2-hydrazono-2,3-dihydro-3-methylbenzthiazole-6-sulphonic acid (S-MBTH) but other substances known for their oxidative coupling ability can also be used in the same way.

The aniline derivatives used according to the present invention contain an acid and a basic group and are, therefore, normally present as internal salts. However, their solubility and handlability can be further improved by using them in the form of salts and especially of alkali metal or ammonium salts. Because of the increased extinction, those compounds are preferred which, in the 3-position to the amine nitrogen, contain an alkyl radical and especially a methyl radical.

These aniline derivatives are either known compounds (cf. J.A.C.S., 78, 5827/1956) or can be prepared in an analogous manner to the known compounds.

As already stated above, the system according to the present invention serves for the detection of hydrogen peroxide or of hydrogen peroxide-producing systems or peroxidases. By hydrogen peroxide-producing systems, there are to be understood, in particular, the substrate/substrate oxidase pairs important in clinical diagnosis in which the substrate is oxidised in the presence of atmospheric oxygen and hydrogen peroxide is produced. Depending upon which of the two components is added to the agent, there can be detected either the substrate or the substrate oxidase. By way of example, there may be mentioned the systems glucose/glucose oxidase, cholesterol/cholesterol oxidase, uric acid/uricase, creatinine/creatininase and sarcosine oxidase. Consequently, the reagent combinations according to the present invention comprise the substrate or substrate oxidase, peroxidase, a chromogen capable of oxidation, as well as one of the compounds of general formula (I) used according to the present invention and possibly also buffers, wetting agents, stabilising agents, activators and the like, either in solution or in an appropriate solid carrier, preferably an absorbent paper. The amounts and composition can be readily determined by the expert on the basis of known similar tests.

Thus, according to the present invention, there is also provided a process for the detection of hydrogen peroxide or of hydrogen peroxide-forming substrates or peroxidases, wherein an agent according to the present invention is brought together with a sample and the coloration is evaluated visually or with a photometer. When the agent is impregnated on to a carrier, the carrier is dipped into a sample and the coloration is determined in known manner. Alternatively, again when the agent is impregnated on to a carrier, the carrier is dipped into a sample until all the reagents are eluted and the coloration is determined with a photometer, possibly after dilution or passing through oxygen.

The following Examples are given for the purpose of illustrating the present invention:

EXAMPLE 1

Determination of hydrogen peroxide in solutions.
Reagent solutions:

| Solution A | Solution B |
| --- | --- |
| 0.2 mmol MBTHS+/liter | 0.2 mmol 4-aminoantipyrine/liter |
| 1 mmol substrate/liter | 1 mmol substrate/liter |
| 200 U peroxidase/liter | 200 U peroxidase/liter |
| 0.1 mol phosphate buffer/liter (pH 7.0) | 0.1 mol phosphate buffer/liter (pH 7.0) |
| 0.5% detergent (fatty alcohol polyglycol ether) | 0.5% detergent |

+ 2-hydrazino-2,3-dihydro-3-methylbenzthiazole-6-sulphonic acid.

2 ml. amounts of these solutions are mixed with 0.05 ml. of a 2 m molar hydrogen peroxide solution, after about 60 seconds well mixed and the extinction measured in 1 cm. cuvettes in a photometer after 5 to 15 minutes.

The following extinctions were determined:

| substrate | MBTHS extinction in mE | | | 4-aminoantipyrine extinction in mE | | |
| --- | --- | --- | --- | --- | --- | --- |
| | λ | 5 min. | 15 min. | λ | 5 min. | 15 min. |
| N,N—di-(hydroxyethyl)-m-toluidine | 585 | 780 | 650 | — | — | — |
| N—ethyl-N—hydroxyethyl-m-toluidine | 580 | 660 | 560 | — | — | — |
| N,N—di-(carboxylatoethyl disodium salt)-m-toluidine | 585 | 753 | 755 | 550 | 424 | 419 |
| N—ethyl-N—sulphoethyl-m-toluidine | 590 | 874 | 873 | 550 | 487 | 483 |
| N—ethyl-N—sulphophenylenemethyl-m-toluidine | 600 | 760 | 758 | 550 | 432 | 425 |
| N—ethyl-N—carboxylatophenylenemethyl-m-toluidine sodium salt | 600 | 738 | 735 | 550 | 463 | 455 |
| N—ethyl-N—sulphophenylenemethylaniline | 600 | 750 | 747 | — | — | — |

Example 2

Determination of uric acid in serum.

Into an appropriate glass vessel which contains 80 ml. of a 0.1 molar potassium phosphate buffer solution (pH 7.0) which is stable for 1 year at 20° C. and which additionally contains 0.5% of detergent and 1 mmol/liter N-ethyl-N-(2-sulphophenylenmethyl)-m-toluidine (ESPT), there is placed a reagent strip of about 120 mm. length and 10 mm. breadth which, in each of 3 zones contains, in meshed-in form, 2 reagent carriers lying on top of one another with a surface area of 10 × 15 mm. The two zones fixed on to the lower end of the reagent strip contain, per reagent carrier, 2.5 mg. methylbenzthiazolone-hydrazone-6-sulphonic acid (MBTHS), together with, in each case, 1.7 mg. potassium ferrocyanide and lying thereabove in each case one reagent carrier containing 6 units of uricase. The third reagent zone contains 2 reagent carriers each with 6 units of uricase, 3 mg. tris/citrate buffer (pH 7) and 20 units of peroxidase (POD). The reagent strip is intensively moved about in the buffer solution for 10 seconds, subsequently left to stand for 5 minutes, again moved about for 10 seconds and the eluted reagent carrier then discarded. A reaction solution is thus obtained with the following composition:

| | |
| --- | --- |
| potassium phosphate buffer pH 7.0 | 0.1 mol/liter |
| ESPT | 1 mmol/liter |
| detergent (fatty alcohol polyglycol ether) | 0.5% |
| MBTHS | 0.2 mmol/liter |
| potassium ferrocyanide | 20 mg./liter |
| uricase | 255 U/liter |
| POD | 470 U/liter |

The uric acid content of serum is determined by adding 0.050 ml. of serum sample to 2 ml. of this reaction solution and, after incubating for 20 minutes at 20° to 25° C., the extinction is determined at Hg 578 nm or on a spectrophotometer at 590 nm against a standard.

EXAMPLE 3

Determination of creatinine in serum. Test components:

| (a) buffer solution: | |
|---|---|
| phosphate buffer (pH 7.5) | 0.1 mol/liter |
| N—ethyl-N—(2-sulphoethyl)-m-toluidine (EST) | 1 mmol/liter |
| detergent | 0.5% |

(b) reagent strip:

reagent strip I, the construction and dimensions of which are described in Example 2 and which contains in one test zone 1.9 mg. MBTHS and 0.64 mg. potassium ferrocyanide and in a further zone 30 U sarcosine oxidase, 300 U creatinase and 30 U peroxidase reagent strip II (dimensions 75×6 mm.) with one 6×6 mm. test zone which contains 30 U creatininase.

Preparation of the reagent solution:

The reagent strip I is moved about for 5 to 10 seconds in 32 ml. of the buffer solution, subsequently left to stand for 5 minutes, again moved about for 5–10 seconds and the eluted reagent carrier then discarded.

Determination batch:

2 ml. of the reagent solution are mixed with 0.05 ml. of sample. After 10 minutes incubation at 20° to 25° C., the extinction ($E_1$) is determined at 578 nm (endogenic creatine).

Subsequently, reagent strip II is eluted into this solution in an analogous manner and the extinction ($E_2$) measured at 578 nm after 25 minutes incubation at 20° to 25° C.

A creatinine standard is used parallel thereto under the same conditions. The concentration (C) is calculated according to:

$$C[\text{mg.}/100 \text{ ml.}] = \frac{\Delta E \text{ sample}}{\Delta E \text{ standard}}$$

$$\Delta E = E_2 - E_1$$

Example 4

Storage stability of substrates.

1 mmolar solutions of the substrates N-ethyl-N-($\beta$-hydroxyethyl)-m-toluidine (EHT) and N-ethyl-N-($\beta$-sulphophenylenmethyl)-m-toluidine (ESPT) in phosphate buffer (pH 7.0) were stressed for 3 weeks at different temperatures and the concentrations then determined by HPLC.

| substrate | weeks of stressing | finding again in % at | | |
|---|---|---|---|---|
| | | 35° C. | 50° C. | 60° C. |
| EHT | 1 | — | 87% | 78% |
| | 2 | — | 86% | 76% |
| | 3 | 89% | 83% | 68% |
| ESPT | 1 | — | 99% | 100% |
| | 2 | — | 100% | 99% |
| | 3 | 99% | 101% | 100% |

Example 5

Detection of glucose in urine.

Filter paper (Whatman No. 6) is impregnated with a solution of the following composition and dried at 40°–60° C.:

| glucose oxidase | 200 mg. |
|---|---|
| peroxidase | 20 mg. |
| morpholinoethanesulphonate (1 molar, pH 6) | 65 ml. |
| ECPT | 200 mg. |
| MBTHS | 200 mg. |
| polyvinylpyrrolidone | 300 mg. |
| ethanol | 30 ml. |
| distilled water | ad 100 ml. |

The test paper reacts with urines which contain from 10 to 100 mg./dl. of glucose to give bright pink-violet to dark blue-violet colour shades.

EXAMPLE 6

Determination of peroxidase

Reagent solvent

| Solvent 1 | |
|---|---|
| S-MBTH | 3.2 mmol/l |
| Sodiumlaurylsulphate | 0.1% |
| 3,3-Dimethylglutaric acid/ NaOH-buffer pH 6,6 | 50 mmol/l |
| Water as solvent | |
| Solvent 2 | |
| ETTS | 10 mmol/l |
| Sodiumperborate | 480 mmol/l |
| DTA | 400 mmol/l |
| Dimethylglutaric acid-buffer pH 6,6 | 50 mmol/l |
| Water as solvent | |

1 ml of solvent 1 and 2 will be mixed with 20 µL sample and after 5 minutes the absorption is read on 588 nm against a reagent standard. The concentration will be estimated by comparing the absorption of known concentrations. Following table shows such comparison values.

| POD/1 Reagent solvent | $\Delta$ E (E Sample-E Standard) |
|---|---|
| 1000 ng | 772 mE |
| 750 ng | 585 mE |
| 500 ng | 381 mE |
| 250 ng | 201 mE |
| 125 ng | 100 mE |
| 50 ng | 42 mE |
| 25 ng | 25 mE |
| 0 ng | 0 mE |

It will be understood that the specification and examples are illustrative but not limitative of the present invention and that other embodiments within the spirit and scope of the invention will suggest themselves to those skilled in the art.

What is claimed is:

1. Composition for the detection of
   (a) hydrogen peroxide or hydrogen peroxide forming substrates, or
   (b) peroxidases or peroxidatively reacting substances, which composition comprises a substrate capable of coupling 2-hydrazono-2,3-dihydro-3-methylbenzthiazole-6-sulfonic acid (S-MBTH), S-MBTH, and
(a) a peroxidase or
(b) hydrogen peroxide and hydrogen peroxide forming substance, wherein the substrate capable of coupling is a compound of the formula

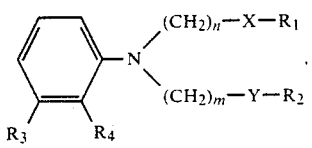 (I)

in which
n and m are individually selected from whole numbers of 1 to 4,
X and Y, which can be the same or different, represent a valence bond or a phenylene radical,
$R_1$ and $R_2$ are individually selected from carboxyl or sulfonic acid groups and one of $R_1$ and $R_2$ can also be hydrogen or lower alkyl,
$R_3$ is alkyl or up to 6 carbon atoms; and
$R_4$ is hydrogen;
or a salt of such compound.

2. Composition as claimed in claim 1, wherein in formula (I) X is a valence bond and Y is a phenylene radical.

3. Composition as claimed in claim 1, wherein in formula (I) X and Y are valence bonds.

4. Composition as claimed in claim 1, wherein in formula (I) X and Y are phenylene radicals.

5. Composition as claimed in claim 1, wherein one of $R_1$ and $R_2$ in formula (I) is carboxyl.

6. Composition as claimed in claim 1, wherein one of $R_1$ and $R_2$ in formula (I) is a sulfonic acid group.

7. Composition as claimed in claim 1, wherein in formula (I) $R_1$ is hydrogen.

8. Composition as claimed in claim 1, wherein in formula (I) $R_1$ is lower alkyl.

9. Composition as claimed in claim 1, wherein the components thereof are impregnated onto an absorbent carrier.

10. Composition as claimed in claim 1, additionally containing a reagent which releases hydrogen peroxide from a hydrogen peroxide forming substrate.

11. Composition as claimed in claim 10, wherein the reagent which forms hydrogen peroxide with the substrate is a substrate oxidase.

12. Method for the detection of
(a) hydrogen peroxide or of hydrogen peroxide forming substrates or
(b) peroxidases or peroxidatively reacting substrates
which method comprises bringing a sample in contact with a composition as claimed in claim 1 and evaluating the coloration obtained as a measure of the content of hydrogen peroxide or hydrogen forming substrate or peroxidase or peroxidatively reacting substrate.

13. Method as claimed in claim 12, wherein said coloration is evaluated visually.

14. Method as claimed in claim 12, wherein said coloration is evaluated with a photometer.

15. Method as claimed in claim 12, wherein the composition is impregnated onto an absorbent carrier and the composite is briefly dipped into a sample until the reagents are eluted, and then determining the coloration.

16. Method as claimed in claim 12, wherein the composition is impregnated onto an absorbent carrier and the composite is briefly dipped into a sample, the coloration being thereafter determined.

17. Method as claimed in claim 16, wherein the coloration is determined after dilution of the reaction mixture or passing same through oxygen.

* * * * *